(12) United States Patent  
Lehtoluoto

(10) Patent No.: US 8,165,698 B2  
(45) Date of Patent: Apr. 24, 2012

(54) FACE MASK

(75) Inventor: Eeva Liisa Lehtoluoto, Kauppapuistikko (FI)

(73) Assignees: Sinikka Anneleena Lehtoluoto, Vaasa (FI); Matti Tapani Lehtoluoto, Vaasa (FI)

( * ) Notice: Subject to any disclaimer, the term of this patent is extended or adjusted under 35 U.S.C. 154(b) by 733 days.

(21) Appl. No.: 12/095,528

(22) PCT Filed: Nov. 29, 2006

(86) PCT No.: PCT/FI2006/050527  
§ 371 (c)(1),  
(2), (4) Date: Dec. 18, 2008

(87) PCT Pub. No.: WO2007/063186  
PCT Pub. Date: Jun. 7, 2007

(65) Prior Publication Data  
US 2010/0241056 A1    Sep. 23, 2010

(30) Foreign Application Priority Data  
Nov. 30, 2005   (FI) ..................................... 20055630

(51) Int. Cl.  
*A61N 1/18* (2006.01)

(52) U.S. Cl. ........................................ 607/140; 604/20

(58) Field of Classification Search .................. 600/392; 604/20; 606/32, 41; 607/3, 66, 76, 139, 607/140, 141, 152, 153  
See application file for complete search history.

(56) References Cited

U.S. PATENT DOCUMENTS

| 3,072,249 | A | * | 1/1963 | Tritsch | 206/441 |
| 4,418,697 | A | | 12/1983 | Tama | 128/640 |
| 4,629,643 | A | | 12/1986 | Curro et al. | 428/131 |
| 5,527,357 | A | * | 6/1996 | Springer, Jr. | 607/140 |
| 5,592,687 | A | | 1/1997 | Lajeunesse | 2/9 |
| 5,765,231 | A | | 6/1998 | Leonard et al. | 2/206 |
| 5,931,859 | A | | 8/1999 | Burke | 607/66 |
| 6,078,842 | A | * | 6/2000 | Gross et al. | 607/152 |
| 6,191,189 | B1 | | 2/2001 | Cinelli et al. | 523/111 |
| 6,694,183 | B1 | * | 2/2004 | Lehtoluoto | 604/20 |
| 7,069,088 | B2 | * | 6/2006 | Lehtoluoto | 607/76 |
| 2004/0089304 | A1 | | 5/2004 | Barakat et al. | 128/206.12 |

FOREIGN PATENT DOCUMENTS

| EP | 0 470 338 A1 | 5/1991 |
| EP | 0 972 460 A1 | 1/2000 |
| FI | 106364 B | 1/2001 |
| WO | WO 98/02126 | 1/1998 |
| WO | WO 00/78388 A1 | 12/2000 |
| WO | WO 2005/004981 A2 | 1/2005 |

* cited by examiner

*Primary Examiner* — Brian T Gedeon  
(74) *Attorney, Agent, or Firm* — Fitzpatrick, Cella, Harper & Scinto

(57) ABSTRACT

A face mask for cleansing of facial skin. The face mask 100 comprises two or more electrodes 22, 23 to which an electric cleansing signal generated by a cleansing signal generator of the face mask is conveyable, the electrodes provided in the face mask 100 being arranged as electrode pairs 24 which comprise a positive electrode 22 and a negative electrode 23 such that all electrode pairs 24 reside in the face mask 100 substantially in the facial area. The face mask is characterized in that the outer edge of the face mask 100 has an edge portion 101 provided with gripping means 120 for fitting the face mask onto the skin of a user of the face mask.

15 Claims, 4 Drawing Sheets

FACE MASK

BACKGROUND OF THE INVENTION

The invention relates to cleansing of skin, and particularly to a face mask for cleansing of facial skin, the face mask being provided with two or more electrodes to be connected to a cleansing signal generator which generates a cleansing signal.

A face mask according to FIG. 1 is previously known, which comprises two or more electrodes 22, 23 to which an electric cleansing signal generated by a cleansing signal generator 1 external to the face mask is conveyable, the electrodes provided in the face mask being arranged as pairs of electrodes comprising a positive electrode and a negative electrode and residing in the face mask. Furthermore, the face mask comprises a fibre layer to be placed against the skin. The fibre material has good absorption properties, enhanced by electric current provided by the electrodes.

The face mask comprises a stiffer outermost portion which presses the face mask against a user's face. The stiffer portion may be tightened against the face e.g. by means of a strip 30 or the like to be fastened behind the head or the ears. The user may find such a strip fastening laborious and inconvenient. In addition, users have different faces, wherefore the stiffer portion does not enable the lower portions to be placed against the skin evenly; therefore, electric current does not become evenly distributed across all the areas to be treated.

BRIEF DESCRIPTION OF THE INVENTION

A purpose of the invention is thus to provide a face mask which fits a user's face well and which, through a cleansing liquid, provides an electric connection between the face mask and the areas to be cleansed. The object of the invention is achieved by a face mask which is characterized by what is disclosed in the independent claims. Preferred embodiments of the invention are disclosed in the dependent claims.

An object of the invention is to provide a face mask for cleansing of facial skin, the face mask comprising an edge portion provided with gripping means for fitting the face mask onto the skin of the user of the face mask. The gripping means enable the face mask to adjust itself to all face types. The gripping means may be made of a suitable adhesive, which is easily removable after use but yet keeps the face mask tightly on the face during use. The adhesive may be dot-like or it may cover the edge portion more extensively.

According to one embodiment, the face mask is provided with an alignment portion to be set at the nose of the user of the face mask. A portion residing between electrodes may include an isolation portion so as to prevent electric current from being transferred between the electrodes, instead of the skin, in the mask. The alignment portion is also equipped with gripping means to enable the face mask to be fitted according to the nose of the user of the face mask. The face mask may even be provided with another alignment portion, e.g. at the chin. The purpose of such an alignment portion provided at the chin in the front part of the face is to enable an opening for the mouth to be adjusted. The face mask is provided with sufficiently large openings at the eyes and the mouth. The openings are larger in an electrically conductive layer in order to prevent the electrically conductive layer of an absorption layer from coming into a direct contact with the users skin or eyes.

According to another embodiment, the edge portion of the face mask is stretchable such that the mask can be tightened while being fitted.

According to yet another embodiment, the structure of the face mask is layered, comprising an absorption layer to be set against the skin, an electrically conductive layer as well as an upper plastic layer which is more extensive than the other layers such that it provides the edges of the face mask with an edge portion which enables the face mask to be fitted onto the users face.

The structure of the face mask is layered, comprising at least an absorption layer and an electrically conductive layer. Furthermore, the electrically conductive layer may be covered by an appropriate outermost surface layer. The surface layer may be a sticky plastic film that can be sprayed onto the electrically conductive layer and the absorption layer such that the sticky plastic film becomes fastened to the electrically conductive layer and the absorption layer. The sprayable plastic film is flexible and thin.

The absorption layer may be made of fibre or of a material which has an absorption property. A fibre weave or a corresponding absorption layer must be able to receive and bind a cleansing liquid in to the absorption layer. It is also possible to replace such a fibre weave with a film. In such a case, the cleansing liquid has to be in a more solid form, e.g. in that of a gel-like cleansing liquid, in order for the cleansing liquid to remain in the face mask during use.

The fibre weave may be made e.g. of a fibre fabric called Fibrella™, which is water needle-punched and binder-free. Such a material provided for healthcare and medical use is also suitable for the material of the mask according to the invention, which is hygienic and sufficiently absorbent.

The absorbent layer is thin. The thickness of the absorbent material is preferably 3 mm or less, more preferably 2 mm or less, and most preferably 1 mm or less. The thin absorption layer can be easily shaped according to the contours of the skin. The thin fibre in itself is light, so it stays on the skin more easily. However, the absorption layer should be sufficiently absorbent and thick so as to be capable of receiving at least an amount of liquid corresponding to the amount of liquid to be transferred into the skin at the beginning of a treatment period. The skin is capable of receiving only a certain amount of liquid. At least this amount of liquid, however, should be absorbed into the fibre so as to prevent the skin from drying due to the treatment period. After the liquid has been transferred into the skin, the thin absorption layer should be dry enough in order to be capable of receiving liquid and impurities back from the moistened skin, assisted by electric current.

The electrically conductive layer may comprise e.g. two or more separate electrodes which have been cut from an aluminium plate. Such plates may be cut and placed in the face mask e.g. such that they reside in the mask at both sides of the nose. When necessary, an aluminium layer plated with a charcoal layer may be used if such a layer is more suitable than an aluminium layer for a user. Alternatively, an aluminium layer may be plated with a precious metal, such as gold or silver.

The electrically conductive layer may be made of silver or a charcoal paste which is attached to the absorption layer e.g. by means of a screen printing method. The electrically conductive layer may also be implemented by printing or etching. The electrodes should be slightly spaced from one another in order to avoid short circuit. The plate-like electrodes may be provided with incisions or they may be perforated in order to ensure that the face mask fits better. The user may then pat the different sections of the plate so that they fit the user's face closely.

The electrodes of the electrically conductive layer may also be netlike. Such netlike electrodes may be provided directly into the fibre e.g. by evaporating or injecting. One comprehensive solution includes two layers of fibre such that one layer is provided with evaporated aluminium. By means of evaporation, the electrically conductive layer can be provided with electrode patterns of different shapes. Such patterns enable certain areas, e.g. the nose or the forehead, to be provided with additional efficiency. The electrode patterns may be provided into the fibre also by screen printing. In addition to aluminium, the electrically conductive layer may be made e.g. of gold, silver of charcoal. The electrically conductive electrodes may also be graphite plates. The electrode portions may also be implemented using nanotechnology such that the molecular structure of plastic has been made to resemble electricity. Such a face mask would be preferable e.g. among those who are allergic to metal. The face mask may be further made to fit better by stiffening the electrically conductive layer at certain places, e.g. the nose area may be provided with a thicker, two-fold electrically conductive layer. It is also possible to use materials of different thicknesses at different points in the face mask.

The topmost layer of the face mask may be a plastic film. The different layers may be attached to one another e.g. by ultrasound. In such a case, the electrically conductive layer resides between the absorption layer and the surface layer. The electrically conductive layer may also be provided directly on the underside of an upper plastic layer. The electrically conductive layer may also be perforated. In such a case, the topmost layer may be attached to the lowest layer by heating the plastic layer such that the topmost layer becomes attached to the lowest absorption layer through the perforations provided in the electrically conductive layer. Such a manner of attachment enables the use of glues to be avoided when attaching the different layers to one another. The attachment may also be implemented by using meltable glue dots, silicon dots, or plastic rivets. The absorption layer and the upper layers may also be attached to one another by the user. In such a case, one layer is provided with a glue portion to receive and attach the layers to one another. Such a gluing procedure implemented by the user may be preferable e.g. when liquid has already been absorbed into the absorption layer.

The topmost plastic layer residing on top of the absorption layer of the face mask may be at least partly moisture permeable, which enhances the drying of the absorption layer during treatment. In such a case, any "excessive" absorption liquid the skin is incapable of receiving may evaporate through the plastic layer outside the face mask. The absorption layer thus becomes dryer, and impurities may be absorbed along with the liquid from the skin into the absorption layer towards the end of the treatment period.

The gripping means may be made of an adhesive which has been covered with a removable cover paper. In addition to the edge portion, the removable cover paper may cover the entire face mask, in which case it keeps the absorption layer clean during storage. A cover paper which covers the entire face mask is preferable particularly when the cleansing liquid has been absorbed into the face mask already while manufacturing the face mask. The cleansing liquid may also be gel-like, so that it sets tightly onto the cover paper, enhancing preservability. Such a gripping procedure may also be implemented by a two-sided sticker tape to be provided in the edge portion.

The face mask may also be a partial face mask. A partial face mask refers to a mask to be placed e.g. on the forehead, or to a face mask to be placed on the nose area. The face mask may be already stretched e.g. at the nose. Furthermore, the thickness of the mask may vary at the nose in order to ensure that the face mask fits better.

The electrodes of the face mask may be provided with electric current from an external device by means of conductor wires. The conductor wires may be provided such that they project from the face mask, or the mask may be equipped with connectors to receive the conductor wires. The connectors may be provided in the lower part of the mask of the face mask, e.g. underneath the chin.

BRIEF DESCRIPTION OF THE DRAWINGS

The invention is now described in closer detail in connection with preferred embodiments and with reference to the accompanying drawings, in which.

DETAILED DESCRIPTION OF THE INVENTION

Figure 1:
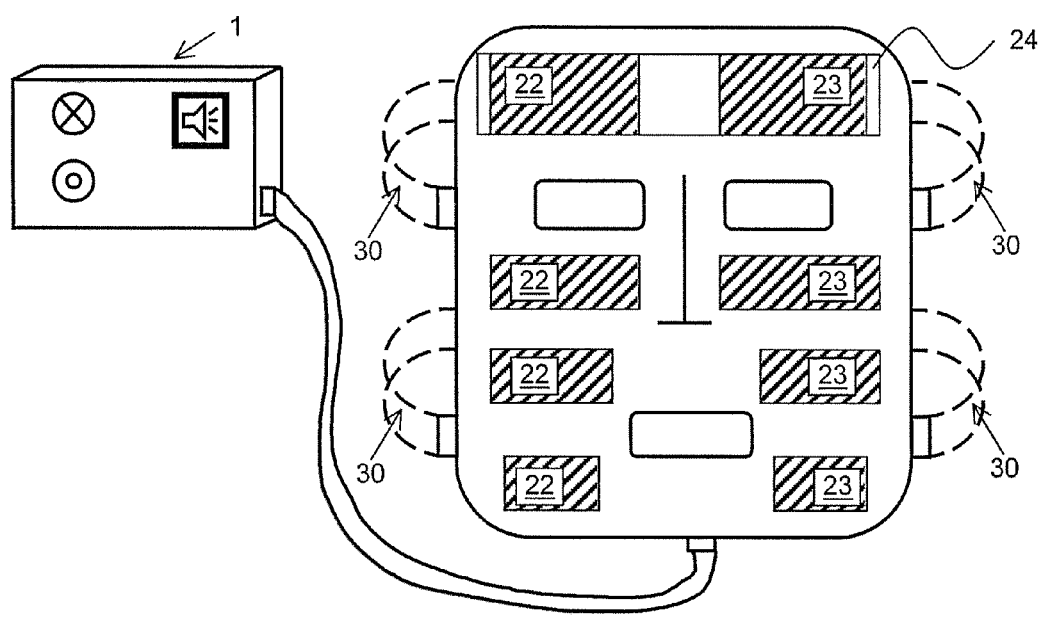
FIG. 1 shows a prior art face mask to be fastened with strips.
Figure 2:
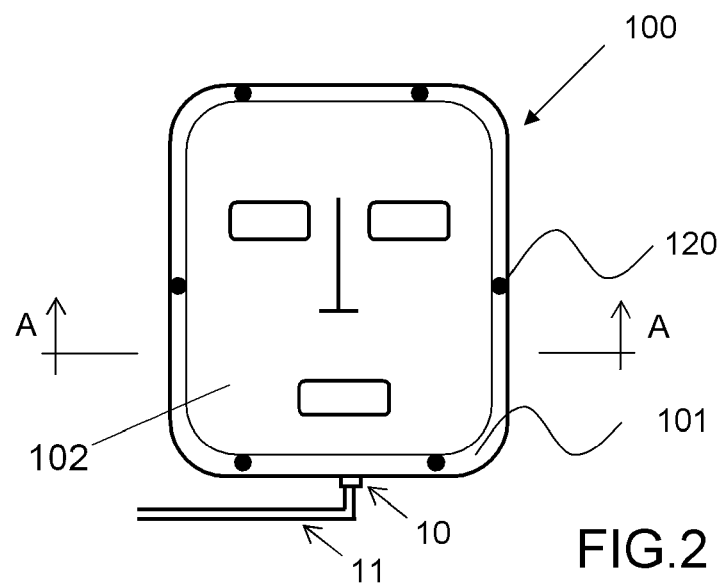
FIG. 2 is a frontal view of a face mask according to the invention.
Figure 2A:
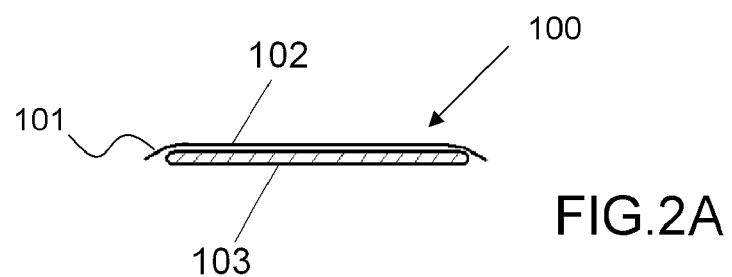
FIG. 2A is a cross-sectional view of the face mask shown in FIG. 2.
Figure 5:
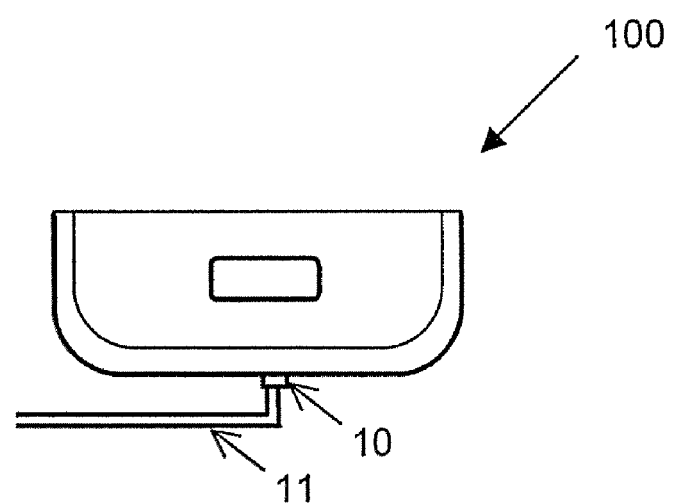
FIG. 5 shows a third embodiment of a face mask according to the present invention.
Figure 6:
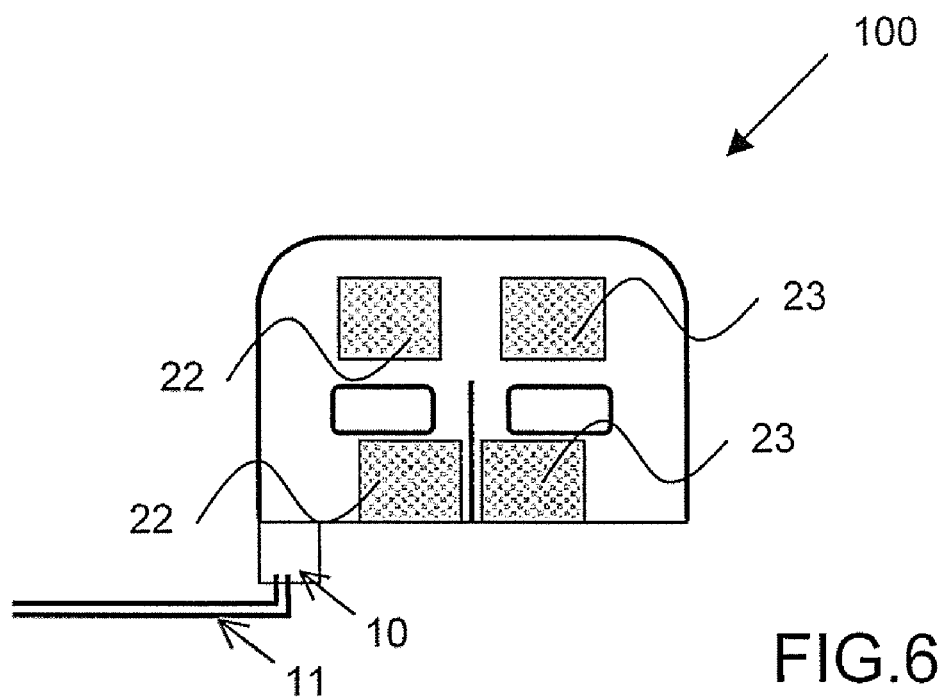
FIG. 6 shows a fourth embodiment of a face mask according to the present invention.
Figure 7:
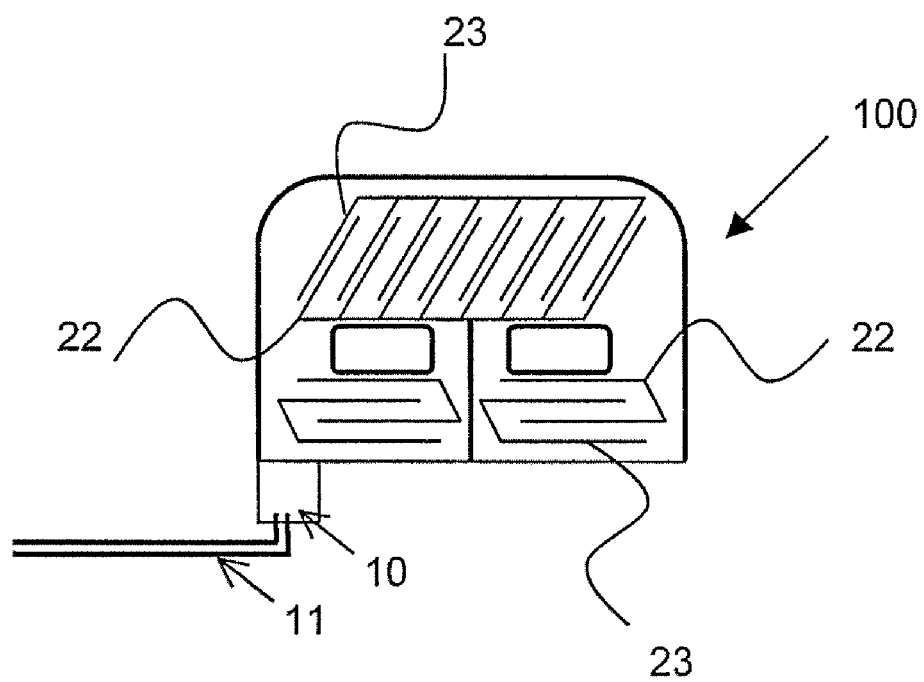
FIG. 7 shows a fifth embodiment of a face mask according to the present invention.

FIG. 2 is a frontal view of a face mask 100 with an uppermost attachment layer 102 and an absorption layer 103, which is to be placed against the skin, of a face mask according to the invention. The face mask 100 includes a connector 10 to which conductor wires 11 are connected. The conductors of electrodes in the face mask may also be provided such that instead of the connector 10, the conductors are connected directly to a cleansing signal generator generating a cleansing signal. The shape of the face mask herein is rectangular, but its shape may vary and be e.g. oval. The size of the face mask 100 may also vary such that it may be a partial face mask 100, covering only a certain area, as illustrated in FIGS. 5 to 7. The outer edge of the face mask 100 has an edge portion 101 provided with gripping means 120 for fitting the face mask onto a user's skin. The edge portion 101 is herein made of stretchable fibre provided with gripping means 120, e.g. glue dots attached to the fibre. The gripping means here comprise six glue dots which enable the face mask to be fastened onto the user's skin. The stretchable edge portion and the gripping means enable the face mask to be fitted closely. The figure shows six glue dots, but their number and size may vary. The edge portion may also be entirely covered with tape-like gripping means, but in such a case they have to yield according to the edge part. The gripping means may also be covered with a removable cover paper. In addition to the edge portion 101, the removable cover paper may also cover the entire face mask, in which case it keeps the absorption layer clean during storage.

Figure 3:
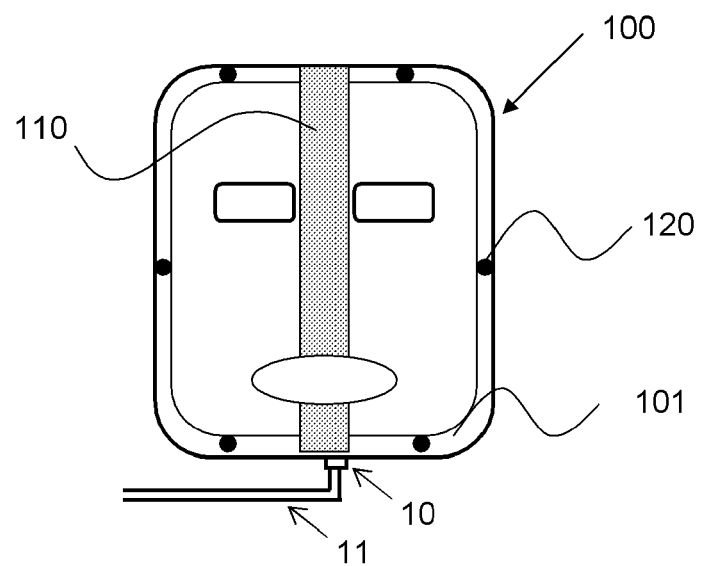
FIG. 3 shows a first embodiment of a face mask according to the present invention.

FIG. 3 shows a first embodiment of a face mask 100 according to the present invention. In addition to the edge portion 101, the face mask herein comprises an isolation portion 110. The purpose of the isolation portion 110 is to prevent electric current from transferring between electrodes, instead of the skin, in the face mask 100. It is to be noted that the size and shape of the isolation portion may vary, depending on the shapes of the electrodes. The edge portion may also be made of a plastic material. In such a case, the uppermost plastic layer is larger than other layers. The face mask can be fitted onto the user's face by means of the stretchable uppermost plastic layer.

Figure 4:
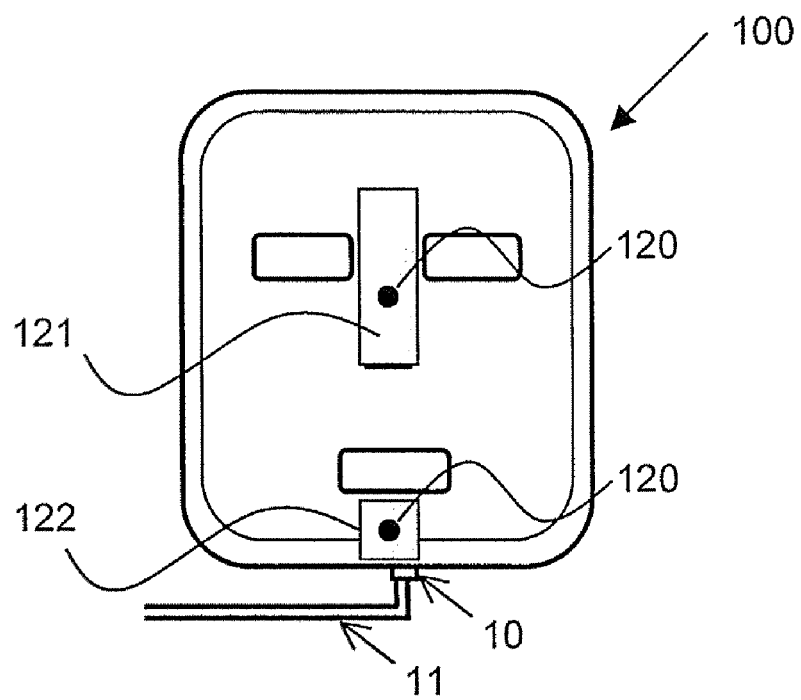
FIG. 4 shows a second embodiment of a face mask according to the present invention.

FIG. 4 shows a second embodiment of a face mask according to the present invention. The face mask 100 is provided with two alignment portions 121 and 122. At the nose of the user, the face mask has a first alignment portion 121 provided with gripping means 120 for adjusting and fitting the face mask according to the nose of the user of the face mask. A second alignment portion 122 is provided at the chin of the user. The purpose of the second alignment portion is to adjust the mouth opening of the face mask at the mouth of the user. The width and length of the alignment portions may vary.

FIG. 5 shows a third embodiment of a face mask according to the present invention. The face mask 100 is a partial face mask such that it covers a certain area of the face. The partial face mask disclosed herein covers a lower part of the face.

FIGS. 6 and 7 show an electrically conductive layer of a face mask according to the invention such that the electrodes can be seen. FIG. 6 shows a fourth embodiment of a face mask according to the present invention. The face mask 100 is a partial face mask such that it covers a certain area of the face. The partial face mask disclosed herein covers an upper part of the face. It is clear that a conductor connection is provided from a connector to electrodes 22 and 23 such that the electric current of the conductors 11 can be conveyed to the electrodes. It is also to be noted that the sizes and shapes of the electrodes 22, 23 may differ from those disclosed in the figure.

FIG. 7 shows a fifth embodiment of a face mask according to the present invention. The lower electrodes in the face mask 100 are strip-like while the upper electrodes overlap in a netlike manner. The strip-like and netlike electrodes may be provided directly in the fibre e.g. by evaporating or injecting. By means of evaporation, the electrically conductive layer can be provided with electrode patterns of different shapes. Such patterns enable certain areas, e.g. the nose area or the forehead area, to be provided with additional efficiency. Further, such patterns enable some point to be provided with no electrodes at all. When necessary, the sides of the forehead, for example, may be provided with no electrodes 22, 23 at all. The electrode patterns may be provided in the fibre also by screen printing.

It is apparent to a person skilled in the art that as technology advances, the basic idea of the invention may be implemented in many different ways. The invention and its embodiments are thus not restricted to the examples described above but may vary within the scope of the claims.

The invention claimed is:

1. A face mask for cleansing of facial skin, the face mask (100) is layered and comprises:
    an absorption layer to be placed against the skin,
    an electrically conductive layer with two or more electrodes (22, 23) to which an electric cleansing signal generated by a cleansing signal generator of the face mask is conveyable, the electrodes (22, 23) being arranged in the face mask (100) as electrode pairs (24) which comprise a positive electrode (22) and a negative electrode (23) such that all electrode pairs (24) reside in the face mask (100), and
    an uppermost attachment layer which is more extensive than the other layers such that it provides edge portion (101) which enables the face mask to be fitted onto the user's face, and wherein the uppermost attachment layer is at least a partly moisture permeable plastic layer that enhances the drying of the absorption layer during cleansing of the facial skin by providing for evaporation of any excess absorption liquid that the skin is incapable of receiving from the absorption layer.

2. A face mask as claimed in claim 1, wherein the edge portion (101) is provided with gripping means (120) for fitting the face mask onto the skin of a user of the face mask.

3. A face mask as claimed in claim 1, wherein the absorption layer is made of a fibre fabric.

4. A face mask as claimed in claim 1, wherein the absorption layer is made of a water needle-punched, binder-free fibre fabric.

5. A face mask as claimed in claim 1, wherein the thickness of the absorption layer is 3 mm or less.

6. A face mask as claimed in claim 1, wherein the thickness of the absorption layer is 2 mm or less.

7. A face mask as claimed in claim 1, wherein the thickness of the absorption layer is 1 mm or less.

8. A face mask as claimed in claim 1, wherein at the nose of the user, the face mask (100) has an alignment portion (121) provided with gripping means (120) for fitting the face mask according to the nose of the user.

9. A face mask as claimed in claim 1, wherein the edge portion (101) has an elasticity property.

10. A face mask as claimed in claim 1, wherein the absorption layer is made of fibre while the electrically conductive layer is implemented by evaporating into the fibre.

11. A face mask as claimed in claim 1, wherein the electrically conductive layer is provided on the underside of the uppermost attachment layer.

12. A face mask as claimed in claim 1, wherein the electrically conductive layer is netlike.

13. A face mask as claimed in claim 1, wherein the electrically conductive layer is perforated.

14. A face mask as claimed in claim 1, wherein the face mask (100) is a partial face mask covering only a certain portion of the user's face.

15. A face mask as claimed in claim 1, wherein the gripping means (120) comprise an adhesive and are equipped with a removable cover paper.

\* \* \* \* \*